United States Patent
Struye et al.

(10) Patent No.: US 6,501,088 B1
(45) Date of Patent: Dec. 31, 2002

(54) METHOD AND APPARATUS FOR READING A RADIATION IMAGE THAT HAS BEEN STORED IN A PHOTOSTIMULABLE SCREEN

(75) Inventors: Luc Struye, Mortsel (BE); Paul Leblans, Kontich (BE)

(73) Assignee: Agfa-Gevaert, Mortsel (BE)

( * ) Notice: Subject to any disclaimer, the term of this patent is extended or adjusted under 35 U.S.C. 154(b) by 53 days.

(21) Appl. No.: 09/595,181

(22) Filed: Jun. 16, 2000

Related U.S. Application Data

(60) Provisional application No. 60/142,276, filed on Jul. 2, 1999, and provisional application No. 60/159,004, filed on Oct. 8, 1999.

(51) Int. Cl.[7] .................. G01T 1/105; G01N 23/04; A61B 6/00; G03C 5/16; G03B 42/08
(52) U.S. Cl. .................. 250/585; 250/581; 250/582
(58) Field of Search .................. 250/581, 582, 250/584, 585, 591

(56) References Cited

U.S. PATENT DOCUMENTS 4,507,562 A * 3/1985 Gasiot et al. ............ 250/484.5
5,028,509 A    7/1991 Shimada et al.

FOREIGN PATENT DOCUMENTS

| EP | 0174875 | * | 6/1990 | ............ C09K/11/61 |
| EP | 0 174 875 |  | 6/1990 |  |
| GB | 0148410 | * | 7/1985 | ............ G01T/1/29 |

* cited by examiner

*Primary Examiner*—Georgia Epps
*Assistant Examiner*—Alicia Harrington
(74) *Attorney, Agent, or Firm*—John A. Merecki; Hoffman, Warnick & D'Alessandro

(57) ABSTRACT

A method and apparatus are provided for reading a radiation image that has been stored in a photostimulable phosphor screen including a divalent europium activated cesium halide phosphor wherein the halide is at least one of chloride and bromide. The screen is scanned by a laser spot having a diameter which is less than 100 micrometer.

4 Claims, 2 Drawing Sheets

METHOD AND APPARATUS FOR READING A RADIATION IMAGE THAT HAS BEEN STORED IN A PHOTOSTIMULABLE SCREEN

This application claims the benefit of copending U.S. Appln. No. 60/142,276 filed Jul. 2, 1999 and Appln. No. 60/159,004 filed Oct. 8, 1999.

FIELD OF THE INVENTION

The present invention relates to a method and a system for reading a radiation image that has been stored in a photostimulable phosphor screen.

BACKGROUND OF THE INVENTION

Radiation image recording systems wherein a radiation image is recorded on a photostimulable phosphor screen by exposing the screen to image-wise modulated penetrating radiation are widely used nowadays.

The recorded image is reproduced by stimulating the exposed photostimulable phosphor screen by means of stimulating radiation and by detecting the light that is emitted by the phosphor screen upon stimulation and converting the detected light into an electrical signal representation of the radiation image.

In several applications e.g. in mammography, sharpness of the image is a very critical parameter.

Sharpness of an image that has been read out of a photostimulable phosphor screen depends not only on the sharpness and resolution of the screen itself but also on the resolution obtained by the read out system which is used.

In conventional read out systems used nowadays a scanning unit of the flying spot type is commonly used. Such a scanning unit comprises a source of stimulating radiation, e.g. a laser light source, means for deflecting light emitted by the laser so as to form a scanning line on the photostimulable phosphor screen and optical means for focussing the laser beam onto the screen.

Examples of such systems are the Agfa Diagnostic Systems, denominated by the trade name ADC 70 and Agfa Compact. In these systems photostimulable phosphor screens are commonly used which comprise a BaFBr:Eu phosphor.

The resolution of the read out apparatus is mainly determined by the spot size of the laser beam. This spot size in its turn depends on the characteristics of the optical light focussing arrangement.

It has been recognised that optimizing the resolution of a scanning system may result in loss of optical collection efficiency of the focussing optics. As a consequence an important fraction of the laser light is not focussed onto the image screen.

A severe prejudice exists against the use of systems having an optical collection efficiency of the focussing optics which is less than 50% because these systems were expected not to deliver an adequate amount of power to the screen in order to read out this screen to a sufficient extent within an acceptable scanning time.

For example in the case of a BaFBr:Eu phosphor a minimal power value of 15 mW on the screen is required to read the image to a sufficient extent within a reasonable time.

Even when all the light emitted by the laser would be captured by the focussing optics, the optical collection efficiency would still not be higher than 50% because of reflections at the optical elements and because of losses at mirrors that are used in the system.

Applying a scanning system that only captures 50% or less of the laser light reduces the collection efficiency to 25% and hence would require the use of a laser which is stronger than 60 mW.

This requirement needs to be complemented by the requirement to have a small emitting area.

Both requirements are hard to solve by means of an inexpensive solution.

OBJECTS OF THE INVENTION

It is an object of the present invention to provide a method and a system for reading a radiation image that has been stored in a photostimulable phosphor screen.

It is a further object of the invention to provide such a method and system that yields a high sharpness.

SUMMARY OF THE INVENTION

The above mentioned objects are realised by a method according to claim 1.

Another aspect of the invention relates to an apparatus as set out in claim 6.

Specific features for preferred embodiments of the invention are set out in the dependent claims.

According to the present invention a screen comprising a divalent europium activated cesium halide phosphor wherein said halide is at least one of chloride and bromide is used. The laser beam which is used to stimulate the screen is focussed so that the spot diameter of the laser spot emitted by that laser, measured between $1/e^2$ points of the gaussian profile of the laser beam, is smaller than 100 micrometer, preferably even smaller than 50 micrometer.

The present invention provides a solution to the prior art problems described in the introductory part of the present invention.

The use of the divalent europium activated cesium halide phosphor allows the use of focussing optics with a low collection efficiency.

In this way the scanning unit can be optimized with regard to small laser spot size on the phosphor screen so that a high resolution system is obtained.

Because the divalent europium activated cesium halide phosphor inherently has a very good optical stimulablility, occasional loss of optical efficiency which originates from the measures taken to obtain a small laser spot size, becomes acceptable. The occasional loss of optical efficiency does not deteriorate the overall image quality obtained in the radiation image read out system, nor does it have a negative effect on the overall throughput of the system.

The photostimulable phosphor screen applied in the present invention comprises a divalent europium activated cesium halide phosphor wherein said halide is at least one of chloride and bromide.

Such a phosphor is known in the art and has for example been disclosed in EP-A-174 875 (and U.S. Pat. No. 5,028, 509). The phosphor is especially well suited for manufacturing 'binderless' phosphor screens. Binderless phosphor screens provide optimal sharpness.

It is advantageous however to use a CsX:Eu phosphor wherein X represents a halide selected from the group consisting of Br and Cl which is obtained by the following method:

mixing CsX with between $10^{-3}$ and 5 mol % of a
    Europium compound selected from the group consisting of EuX'$_2$, EuX'$_3$ and EuOX', X' being a member selected from the group consisting of F, Cl, Br and I, firing the mixture at a temperature above 450° C.

cooling said mixture and recovering the CsX:Eu phosphor.

A phosphor that has been obtained as a result of the above method of preparation has an increased conversion efficiency compared to the state of the art divalent europium activated cesium halide phosphor. The phosphor can be stimulated by means of a lower amount of stimulating light energy.

A photostimulable phosphor screen using such a phosphor is preferably obtained by the method of preparing said CsX:Eu phosphor by firing a mixture of said CsX with between 10-3 and 5 mol % of an Europium compound selected from the group consisting of EuX'$_2$, EuX'$_3$ and EuOX', X' being a halide selected from the group consisting of F, Cl, Br and I and applying said phosphor on a substrate by a method selected from the group consisting of physical vapor deposition, thermal vapor deposition, chemical vapor deposition, radio frequency deposition and pulsed laser deposition.

This method of preparation is advantageous because it allows to deposit the phosphor in the form of needle-shaped crystals. These needle-shaped phosphor crystals act as light guides so that they reduce the lateral spreading of light in the phosphor layer. Reduced lateral light spread leads to images of higher resolution.

Alternatively a phosphor screen containing a CsX:Eu stimulable phosphor, wherein X represents a halide selected from the group consisting of Br and Cl can also be manufactured by performing the steps of:

bringing multiple containers of said CsX and an Europium compound selected from the group consisting of EuX'$_2$, EuX'$_3$ and EuOX', X' being a halide selected from the group consisting of F, Cl, Br and I in condition for vapor deposition and depositing, by a method selected from the group consisting of physical vapor deposition, thermal vapor deposition, chemical vapor deposition, electron beam deposition, radio frequency deposition and pulsed laser deposition, both said CsX and said Europium compound on a substrate in such a ratio that on said substrate a CsX phosphor, doped with between $10^{-3}$ and 5 mol % of an Europium compound, is formed.

This method of preparation is advantageous because it likewise allows to deposit the phosphor in the form of needle-shaped crystals. These needle-shaped phosphor crystals act as light guides so that they reduce the lateral spreading of light in the phosphor layer. Reduced lateral light spread leads to images of higher resolution.

The above phosphors and screen preparation methods have been described in the following U.S. provisional applications which are incorporated by reference into the present application: Nos. 60/159,004 and 60/142,276.

Further advantages and embodiments of the present invention will become apparent from the following description and drawings.

DETAILED DESCRIPTION

The performance of a system is commonly indicated by means of the SWR value. An SWR value indicates the attenuation of a square wave by the system. The amplitude of a very low frequency (0.025 line pairs per mm) (lp/mm) is taken as 100% reference point.

Most digital systems based on a photostimulable phosphor such as BaFBr:Eu lead to an SWR value of 0.15 to 0.20 for 3 line pairs per mm (lp/mm).

Even in case of a very thin, high resolution screen an SWR value of not more than 0.25 is obtained at 3 lp/mm.

For application of a system in the field of mammography the SWR should be of the order of 0.5 at 3 lp/mm.

These SWR values can only be obtained if the laser beam is focussed to a very small value, typically in the order of 50 micrometer or smaller. (The diameter is measured between the $1/e^2$ points of the Gaussian profile of the laser beam).

Hereinafter the fact that a prejudice exists against decreasing the spot diameter of the laser spot to a large extent because such a decrease inherently brings forth a decrease of the laser power at the location where the laser spot scans the photostimulable phosphor screen, is explained. Such a decrease of the laser power might result in the need for increasing the scan time which has a negative influence on the throughput of the system or might result in an insufficient release of the energy stored in the photostimulable phosphor screen.

This fact is explained with reference to a conventional flying spot scanning system wherein a laser diode is used as a light source for stimulating a BaFBr:Eu fosfor screen (prior art system). The laser beam is deflected by means of a mirror galvanometer or a rotating polygon mirror.

Focussing a laser beam to a small diameter is easy in case the focussed spot is stationary and in case it is not used for scanning and in case the distance from the focussing lens to the focus is small.

In a flying spot scanner however, the beam is deflected along a distance of typically 400 mm (length of a scan line). A mirror galvanometer or a rotating polygon mirror is used to deflect the beam in the direction of the scan line. The scanning beam can be deflected within an angle from ca. −20° to +20° (This angle will be referred to as the angle θ).

For this reason the length of the scanline Ls is determined by the distance from the galvanometer to the photostimulable phosphor screen (distance b) and the angle θ.

Figure 1:
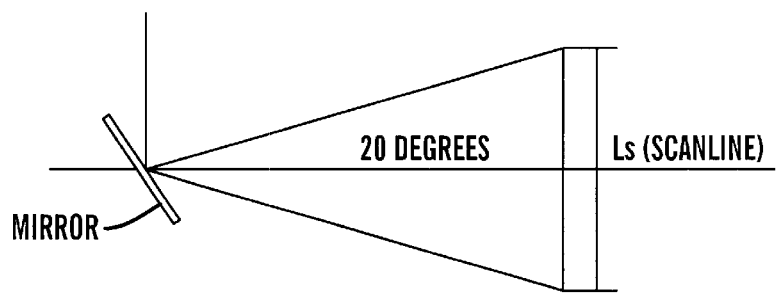
FIG. 1 illustrates the set up of a scanning system.
Figure 2:
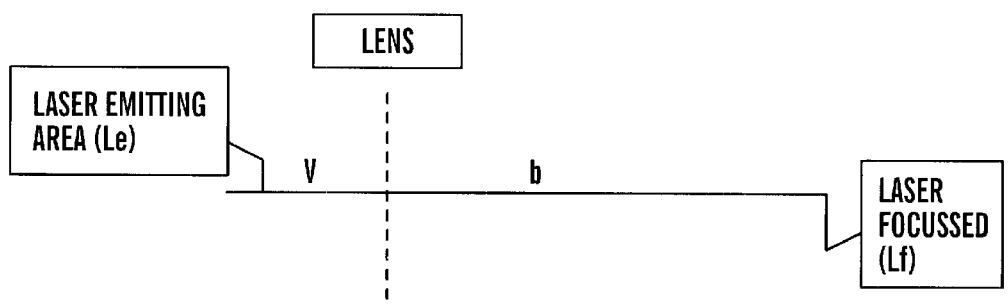
FIG. 2 is an illustration of the image and object distance b and v.

The following formulae apply. (see also FIG. 1).

$$Ls < 2*b*tg(2\theta)$$

or $$b > \frac{Ls}{2*tg(2\theta)}$$

$$b > \frac{400}{2*tg(2\theta)} = 549.5 \text{ mm}$$

To obtain a scan line with a length of 400 mm, the distance to the screen must be larger than ca. 550 mm.

In practice a minimum distance of 600 mm is needed between the focussing lens and the photostimulable phosphor screen.

Furthermore the fact that the laserbeam is focussed by means of a lens has to be taken into account. Using the formulae of classical optics the optical collection efficiency of the foccussing set up and the maximum allowed emitting area can be calculated in function of the optical parameters of the used lenses.

In the case a single lens is used to focus the following formulas can be used.

The relation between the laser emitting area (Le) and the spotsize in focus (Lf) is given by the equation:

$$\frac{1}{f} = \frac{1}{v} + \frac{1}{b} \quad \text{and}$$

$$Le = Lf * \frac{v}{b}$$

In the practical situation b is larger than 600 mm (see higher).

The optical transmission is determined by the diameter of the lens and the divergence of the laser.

When considering a system wherein a diode laser is used the fact that these diode lasers are normally astigmatic showing divergences of 10° and 30° has to be taken into consideration.

Lenses are normally limited to a diameter of ca. 30 mm in order to obtain a good modulation transfer function (MTF). To collect all the light in an angle of 30° within a lens of 30 mm the maximum distance 'v' is 15/(tg 30) or 26 mm.

Lf is already determined by the maximum diameter of 50 $\mu$m.

The maximum emitting area can be calculated as:

$$Le = Lf * \frac{v}{b}$$

$$Le = 50 * \frac{26}{600} = 2.17 \, \mu m$$

This is below the limit of what can be reached with single diode lasers. Mostly the emitting area is not smaller than 3 $\mu$m.

Calculating the spot size of the focussed laser beam in this way only takes into account the rules of the classical optics. In practice the spot size will be larger as calculated by this way because the beam is diffraction limited.

In practice it is good that the spot size is determined by the diffraction limited gaussian laws and not by the magnification calculated with the classical lens formula. This is only possible when the spotsize calculated with the lens formula is smaller to a large extent than the spotsize calculated with the theory for the diffraction limited gaussian beam. This means that Lf should be as low as possible and preferably below 20 $\mu$m.
Because $$Le = Lf * \frac{v}{b}$$

$$Lf = Le * \frac{b}{v}$$

Since Le is limited to 3 $\mu$m and b is limited to 600 mm, the only possibility to obtain a small Lf value is to increase v.

To reach a theoretical spot size of 20 micrometer, the distance v between the lens and the laser should be at least 90 mm as is shown by the following equations.

$$v = \frac{Le}{Lf} * b$$

$$v = \frac{3}{20} * 600$$

$$v = 90 \text{ mm}$$

However, at a distance of at least 90 mm quite a lot of light is lost and the optical efficiency is low.

The optical efficiency will be calculated assuming a divergence of 10° in one direction and 30° in the other direction.

The diameter of the laser beam at the position of the lens is 2*90*tg(10°)=32.7 for one direction and 2*90*tg(30°)= 104 mm for the other direction.

For a lens with a diameter of 30 mm, losses will be 30/32.7=92% of the laser light in one direction and 30/104= 29% in the other direction.

The optical efficiency of the described set up is then 0.29*0.92=26%.

Due to reflections at the surface of the lenses and mirrors another 50% of the light is lost. The resulting optical efficiency is therefore 26%*0.5=13%. In order to obtain 15 mW at the photostimulable phosphor screen in the described set up the laser should have an emitting power of 15/0.13= 115 mW.

Laser diodes of emitting such an amount of power cannot be easily obtained at reasonable cost.

In case a BaFBr:Eu phosphor is used, and therefore no extra losses of optical efficiency are allowed, the minimal spotsize which can be accepted can be calculated by Le=Lf*(v/b)

Lf=Le*(b/v)

Le is limited to 3 $\mu$m (smallest available emitting area of a diode laser), b equals 600 mm (smallest distance between lens and phosphor screen which allows deflection of the laser spot along a scan line of a length of 400 mm), v equals 26 mm (smallest distance between laser and lens to collect all the light of the laser).

The minimum theoretical value of Lf is equal to 3*600/ 26=69.2 $\mu$m.

In practice the spot size will be a little larger because of the non ideal behaviour of the optics (e.g. gaussian aberation of the lens and limited flatness of the deflection mirror).

The spotsize will also be larger because of the diffraction gaussian limiting effects.

Taking all these effects into account will result in a minimum spotsize of 100 micrometer in case a BaFBr:Eu phosphor would have been used.

In accordance with the present invention a stimulable phosphor screen comprising a divalent europium activated cesium halide phosphor wherein said halide is at least one of chloride and bromide, is used.

Most preferably a needle shaped divalent cesium halide phosphor as described higher is used. This needle shaped phosphor has as an intrinsic SWR value of 0.6 to 0.65 at 3 line pairs per mm. This implies that the SWR value of the read out apparatus should be approximately 0.7 for 3 linepairs per mm, or 0.5 for 5 line pairs per mm.

Such SWR values can be obtained if the laser beam is focussed down to 50 $\mu$m. (This diameter being measured between the $1/e^2$ points of the gaussian profile of the laser beam).

Measurements:

To determine the minimum laser power needed in the read out apparatus, the parameter Se is defined as the amount of laser energy needed to release 63% of the stored energy as emission light within an area of 1 mm$^2$.

The laser power needed is given by:

$$Pl = Se * Area\_IP/T$$

Where Pl is the laser Power, Area_IP represents the total area of the image plate to be read out and T represents the total amount of time required to read out the photostimulable phosphor screen.

The laser power Pl is proportional with Se.

For a BaFBr:Eu phosphor the value for Se=17 uJ/mm$^2$.

For a CsBr:Eu according to the present invention the value for Se=6 $\mu$J/mm$^2$.

The laser power required at the surface of the phosphor screen in case of a CsBr:Eu phosphor is thus 6/17 of the laser power required in case of a BaFBr:Eu phosphor in order to attain a comparable result.

Whereas in case of a BaFBr:Eu phosphor a power of 15 mW was required on the screen, in case of a CsBr:Eu phosphor only about 5 mW is required on the screen.

Experiments have proven that even with 2 mW (power value on the screen) read out of a screen within an acceptable amount of time can be obtained.

The use of this phosphor thus allows to use of a low power laser and a small laser spot size (resulting in enhanced resolution) even if this optimization leads to low optical efficiency.

The use of this phosphor furthermore allows to work with an object distance which is smaller than 30 mm (e.g. 26 mm, see higher).

Figure 3:
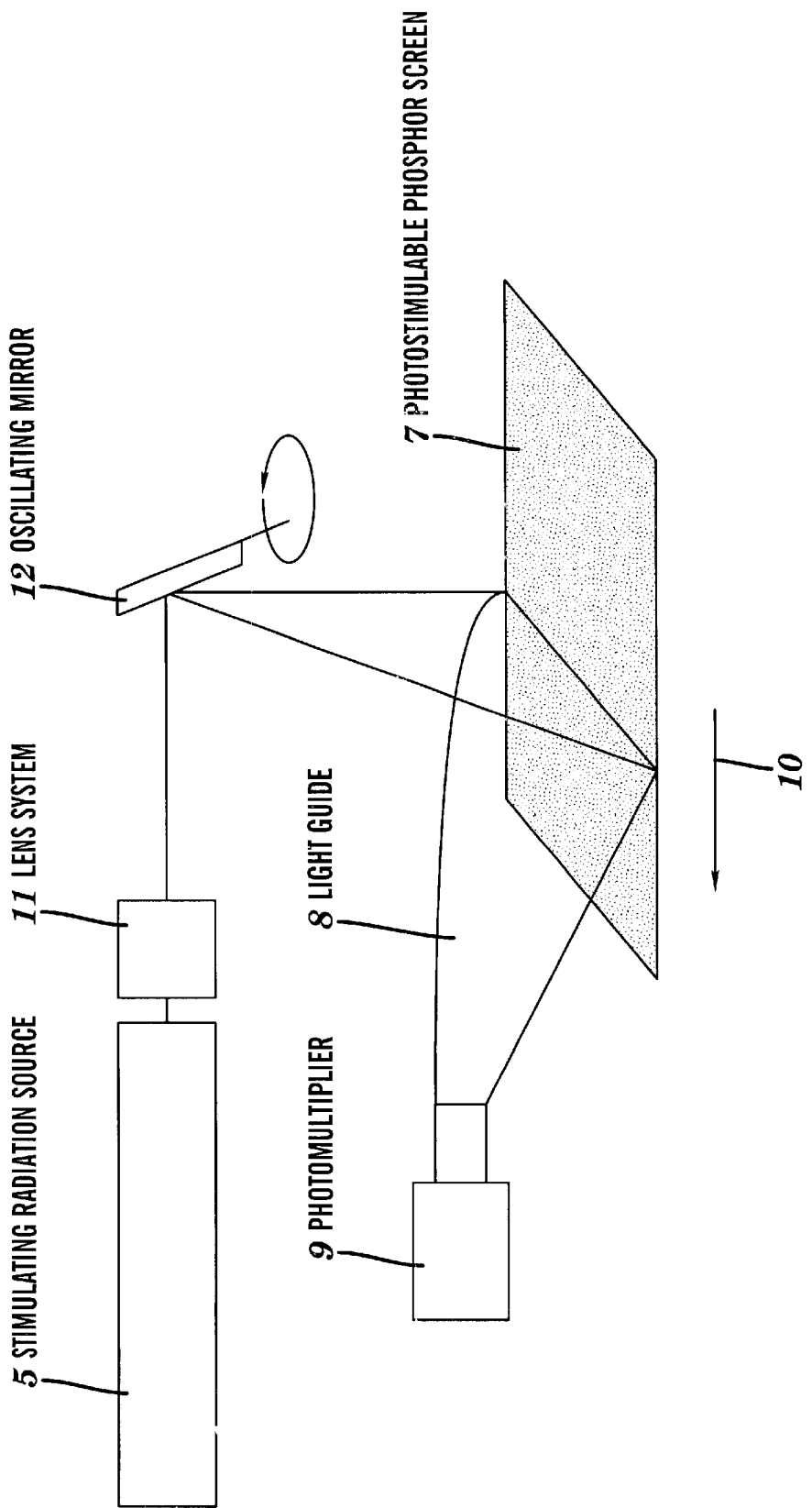
FIG. 3 is an illustration of an apparatus according to the present invention.

An embodiment of an apparatus according to the present invention has been shown in FIG. 3.

The read out unit comprises a source of stimulating radiation (5), more particularly a diode laser of the following type SDL-7601-V1 of Spectra Diode Labs. The laser emits at 680 nm and has an optical power of 10 mW. The emitting dimensions are 3 $\mu$m×1 $\mu$m.

The unit further comprises a lens system (11), an oscillating mirror (12) for deflecting light emitted by the stimulating laser source onto the photostimulable phosphor screen (7) into the scan direction, a light guide (8) for guiding light emitted by the photostimulable phosphor screen upon stimulation onto a photomultiplier (9).

The read out unit further comprises means for transporting (not shown) the photostimulable phosphor screen into the sub-scan direction indicated by arrow (10).

The lens system is arranged so that the object distance is 90 mm and the image distance is 600 mm.

What is claimed is:

1. A method for reading a radiation image that has been stored in a photostimulable phosphor screen comprising the steps of
    scanning said screen by means of stimulating radiation emitted by a laser source,
    detecting light emitted by said screen upon stimulation,
    converting detected light into an electrical signal representation of said radiation image, wherein
        said photostimulable phosphor screen comprises a divalent europium activated cesium halide phosphor wherein said halide is at least one of chloride and bromide, said phosphor being obtained by the steps of:
            mixing CsX, wherein X represents a halide selected from the group consisting of Cl and Br, with between 10$^{-3}$ and 5 mol % of a Europium compound selected from the group consisting of EuX'$_2$, EuX'$_3$ and EuOX', X' being a member selected from the group consisting of F, Cl, Br and I,
            firing the mixture at a temperature above 450° C.,
            cooling said mixture, and
            recovering the CsX:Eu phosphor, and wherein
                said laser beam is focused so that the spot diameter of the laser spot emitted by said laser, measured between 1/e$^2$ points of the gaussian profile of said laser beam is smaller than 100 micrometer.

2. A method according to claim 1 wherein said spot diameter is smaller than 50 micrometer.

3. A method according to claim 1 wherein said phosphor screen is obtained by the steps of
    preparing said CsX:Eu phosphor by firing a mixture of said CsX with between 10$^{-3}$ and 5 mol % of an Europium compound selected from the group consisting of EuX'$_2$, EuX'$_3$ and EuOX', X' being a halide selected from the group consisting of F, Cl, Br and I, and
    applying said phosphor on a substrate by a method selected from the group consisting of physical vapour deposition, thermal vapour deposition, chemical vapour deposition, radio frequency deposition and pulsed laser deposition.

4. A method according to claim 1 wherein said phosphor screen is obtained by the steps of
    bringing multiple containers of said CsX and an Europium compound selected from the group consisting of EuX'$_2$, EuX'$_3$ and EuOX', X' being a halide selected from the group consisting of F, Cl, Br and I in condition for vapour deposition, and
    depositing, by a method selected from the group consisting of physical vapour deposition, thermal vapour deposition, chemical vapour deposition, electron beam deposition, radio frequency deposition and pulsed laser deposition, both said CsX and said Europium compound on a substrate in such a ratio that on said substrate a CsX phosphor, doped with between 10$^{-3}$ and 5 mol % of an Europium compound, is formed.

* * * * *

UNITED STATES PATENT AND TRADEMARK OFFICE
Certificate

Patent No. 6,501,088 B1                                            Patented: December 31, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Luc Struye, Mortsel, Belgium; Paul Leblans, Kontich, Belgium; Martin Devenney, Mountain View, CA; and Casper Reaves, San Jose, CA.

Signed and Sealed this Sixth Day of July 2004.

GEORGIA Y. EPPS
*Supervisory Patent Examiner*
Art Unit 2873